United States Patent [19]

Crivello

[11] 4,310,469

[45] Jan. 12, 1982

[54] DIARYLIODONIUM SALTS

[75] Inventor: James V. Crivello, Clifton Park, N.Y.

[73] Assignee: General Electric Company, Schenectady, N.Y.

[21] Appl. No.: 117,726

[22] Filed: Feb. 1, 1980

Related U.S. Application Data

[60] Division of Ser. No. 974,497, Dec. 29, 1978, abandoned, which is a continuation-in-part of Ser. No. 638,983, Dec. 9, 1975, which is a continuation of Ser. No. 466,375, May 2, 1974, abandoned.

[51] Int. Cl.$^3$ ............................................. C07F 9/90
[52] U.S. Cl. .................................. 260/446; 260/440; 260/447; 568/8; 568/16
[58] Field of Search .................. 260/446, 440, 447; 568/8, 16

[56] References Cited

U.S. PATENT DOCUMENTS

| | | | |
|---|---|---|---|
| 3,585,227 | 6/1971 | Dreyfuss | 260/440 |
| 3,981,897 | 9/1976 | Crivello | 260/446 X |
| 4,058,400 | 11/1977 | Crivello | 260/440 X |
| 4,069,055 | 1/1978 | Crivello | 260/446 X |
| 4,136,102 | 1/1979 | Crivello | 260/446 X |
| 4,161,478 | 7/1979 | Crivello | 260/446 X |

FOREIGN PATENT DOCUMENTS 1516351 7/1978 United Kingdom .
1516352 7/1978 United Kingdom .

*Primary Examiner*—Helen M. S. Sneed
*Attorney, Agent, or Firm*—William A. Teoli; James C. Davis, Jr.

[57] ABSTRACT

Cationic polymerization of epoxy monomers or prepolymers can be achieved by use of certain radiation sensitive aromatic halonium salts. Curable compositions are provided which can be used as sealants, coating compounds, encapsulants, etc.

2 Claims, No Drawings

DIARYLIODONIUM SALTS

This is a division, of application Ser. No. 974,497, filed Dec. 29, 1978, abandoned which is a continuation-in-part of my copending application Ser. No. 638,983, filed Dec. 9, 1975, which is a continuation of Ser. No. 466,375, filed May 2, 1974, now abandoned, which are assigned to the same assignee as the present invention.

The present invention relates to epoxy resin compositions which can be cured by exposure to radiant energy.

Epoxy resins have generally been employed in a variety of applications requiring high performance materials. Cure of an epoxy resin can generally be achieved by two package systems based on the incorporation into the resin of active amine containing compounds or carboxylic acid anhydrides. These systems require thorough mixing of the ingredients; in addition, cure time can be several hours.

Another catalyst which can be used to cure epoxy resins as "one package" systems is based on the employment of a Lewis Acid catalyst in the form of an amine complex such as boron trifluoride-monoethyl amine. The Lewis Acid is released on heating; cure takes place within 1 to 8 hours and can require a temperature of 160° C. and higher. As a result, these one package epoxy compositions cannot be employed to coat heat sensitive devices such as delicate electronic components. Nor can epoxy monomers having low boiling points be used due to the resulting losses to evaporation during cure.

As shown by Schlesinger, U.S. Pat. No. 3,703,296, certain photosensitive aromatic diazonium salts can be employed to cure epoxy resins. When photolyzed, these aromatic diazonium salts are capable of releasing, in situ, a Lewis Acid catalyst which can initiate the rapid polymerization of the epoxy resin. However, even though these one package epoxy resin mixtures can provide fast curing compositions, a stabilizer must be used to minimize cure in the dark during storage of these mixtures. Despite these measures, gellation of the mixture can occur even in the absence of light. In addition, nitrogen is released during UV-cure, which can result in film imperfections. Diazonium salts are generally thermally unstable, rendering the use of such materials hazardous because of the possibility of run-away decomposition.

The present invention is based on the discovery that certain radiation sensitive aromatic halonium salts, for example

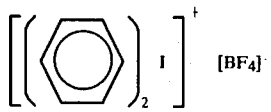

can be incorporated into epoxy resins to provide one-package radiation curable compositions which do not require a stabilizer to minimize cure at ambient temperatures during the shelf period, and are free of all the aforementioned disadvantages of the above described diazonium salt compositions.

Included among the radiation sensitive aromatic halonium salts which can be used to make the curable compositions of the present invention are compounds of the formula, $$[(R)_a(R^1)_bX]_c^+ [MQ_d]^{-(d-e)} \quad (1)$$

where R is a monovalent aromatic organic radical, $R^1$ is a divalent aromatic organic radical, X is a halogen radical such as I, Br, Cl, etc., M is a metal or metalloid and Q is a halogen radical such as Cl, F, Br, I, etc., a is a whole number equal to 0 or 2, b is a whole number equal to 0 or 1, and when a is 0, b is 1, and when b is 0, a is 2.

c = d − e e = valence of M and is an integer equal to 2 to 7 inclusive, and d is > e and is an integer having a value up to 8.

Radicals included by R can be the same or different, aromatic carbocyclic or heterocyclic radicals having from 6 to 20 carbon atoms, which can be substituted with from 1 to 4 monovalent radicals selected from $C_{(1-8)}$ alkoxy, $C_{(1-8)}$ alkyl, nitro, chloro, etc., R is more particularly, phenyl, chlorophenyl, nitrophenyl, methoxyphenyl, pyridyl, etc. Radicals included by $R^1$ are divalent radicals such as

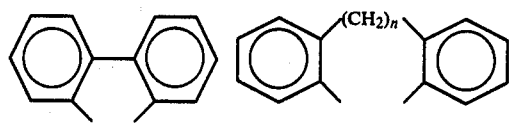

etc. Metal or metalloids included by M of formula I are transition metals such as Sb, Fe, Sn, Bi, Al, Ga, In, Ti, Zr, Sc, V, Cr, Mn, Cs, rare earth elements such as the lanthanides, for example, Cd, Pr, Nd, etc., actinides, such as Th, Pa, U, Np, etc. and metalloids such as B, P, As, etc. Complex anions included by $MQ_d^{-(d-e)}$ are, for example, $BF_4^-$, $PF_6^-$, $AsF_6^-$, $SbF_6^-$, $FeCl_4^=$, $SnCl_6^-$, $SbCl_6^-$, $BiCl_5^=$, etc.

Halonium salts included by formula (1) are, for example,

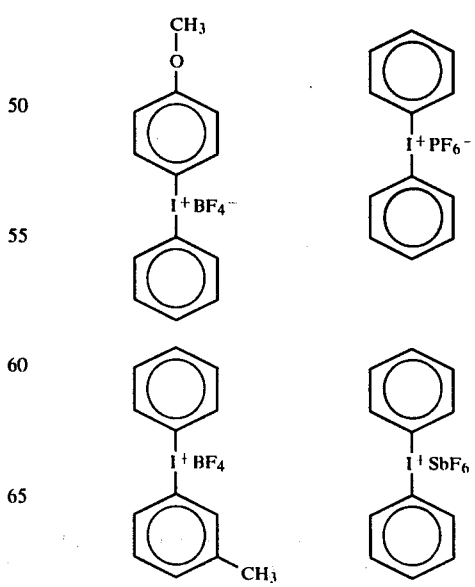

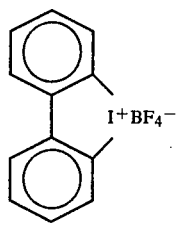

There is provided by the present invention curable epoxy compositions comprising, (A) an epoxy resin polymerizable to a higher molecular weight state selected from epoxy monomer, epoxy prepolymer, oxirane containing organic polymer and mixtures thereof, and (B) an effective amount of a radiation sensitive aromatic halonium salt capable of effecting the cure of (A) by release of a Lewis Acid catalyst when activated by radiant energy.

The halonium salts of formula (1) are well known and can be made by the procedures described by O. A. Ptitsyna, M. E. Pudecva, et al, Dokl., Adad. Nauk, SSR, 163 383 (1965); Dokl., Chem., 163 671 (1965). F. Marshall Beringer, M. Drexler, E. M. Gindler, etc. J. Am. Chem. Soc., 75 2705 (1953).

The term "epoxy resin" as utilized in the description of the curable compositions of the present invention, includes any monomeric, dimeric or oligomeric or polymeric epoxy material containing one or a plurality of epoxy functional groups. For example, those resins which result from the reaction of bisphenol-A (4,4'-isopropylidenephenol) and epichlorohydrin, or by the reaction of low molecular weight phenol-formaldehyde resins (Novolak resins) with epichlorohydrin, can be used alone or in combination with an epoxy containing compound as a reactive diluent. Such diluents as phenyl glycidyl ether, 4-vinylcyclohexene dioxide, limonene dioxide, 1,2-cyclohexene oxide, glycidyl acrylate, glycidyl methacrylate, styrene oxide, allyl glycidyl ether, etc., may be added as viscosity modifying agents.

In addition, the range of these compounds can be extended to include polymeric materials containing terminal or pendant epoxy groups. Examples of these compounds are vinyl copolymers containing glycidyl acrylate or methacrylate as one of the comonomers. Other classes of epoxy containing polymers amenable to cure using the above catalysts are epoxy-siloxane resins, epoxy-polyurethanes and epoxy-polyesters. Such polymers usually have epoxy functional groups at the ends of their chains. Epoxy-siloxane resins and method for making are more particularly shown by E. P. Plueddemann and G. Fanger, J. Am. Chem. Soc. 81 632-5 (1959).

I have found that the aromatic halonium salts of formula (1), are not often compatible with the above described epoxy-siloxanes which can comprise 50 to 99.99 mole percent of organosiloxane units of the formula,

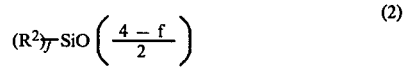

chemically combined with 0.01 to 50 mole percent of epoxy siloxane units of the formula,

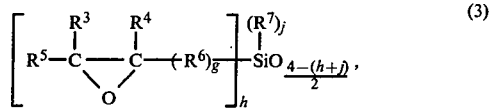

where $R^2$ is a monovalent organic radical selected from the class consisting of $C_{(1-13)}$ hydrocarbon radicals, substituted $C_{(1-13)}$ hydrocarbon radicals, cyanoalkyl radicals, and perfluoroalkyl radicals, $R^3$ and $R^4$ are monovalent radicals selected from hydrogen and $C_{(1-8)}$ alkyl radicals, $R^5$ is selected from hydrogen, $C_{(1-8)}$ alkyl radicals and $C_{(1-8)}$ alkylene radicals, $R^6$ is a divalent radical selected from $C_{(1-8)}$ alkylene radicals, $C_{(1-8)}$ alkylene ether radicals and $C_{(4-8)}$ carbalkoxy radicals, and when $R^5$ is divalent, it can be part of a cycloaliphatic ring structure with $R^6$, $R^7$ is selected from $R^2$ radicals, f is a whole number equal to 0 to 3 inclusive, g is a whole number equal to 0 or 1, h is an integer equal to 1 to 3 inclusive and j is a whole number equal to 0 to 2 inclusive.

Radicals included by $R^2$ and $R^7$ are, for example, $C_{(1-8)}$ alkyl radicals such as methyl, ethyl, propyl, butyl, pentyl, hexyl, heptyl octyl; haloalkyl radicals such as chloroethyl, bromobutyl perfluoropropyl, etc.; $C_{(6-13)}$ aromatic radicals such as phenyl, tolyl, xylyl, naphthyl, etc.; haloaryl such as chlorophenyl, bromotolyl, etc.; cyanoethyl, cyanopropyl, etc. Radicals included by $R^3$ and $R^4$ are in addition to hydrogen, the $C_{(1-8)}$ alkyl radicals of $R^2$. Radicals included by $R^5$ and hydrogen, the $C_{(1-8)}$ alkyl radicals of $R^2$ and $C_{(1-8)}$ alkylene radicals such as methylene, dimethylene, trimethylene, etc. Radicals included by $R^6$ include the divalent alkylene radicals of $R^5$, $[(CH_2)_qO(CH_2)_r]_s$, where q, r and s are integers having the value of 1 to 3 inclusive, and carbalkoxy radicals such as

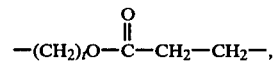

where t has a value of 1 to 4 inclusive, and when $R^5$ is divalent it can form cycloaliphatic radicals with $R^6$, such as

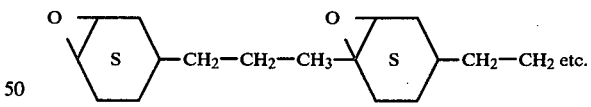

Methods for making the epoxy-siloxanes consisting essentially of chemically combined units of formulas (2) and (3) are shown by Plueddemann et al cited above and Merrill Cohen U.S. Pat. No. 3,219,624 assigned to the same assignee as the present invention. There can be used, for example, hydrosilation of organopolysiloxanes consisting essentially of formula (2) units chemically combined with siloxane units of the formula,

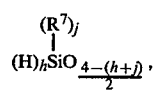

where $R^7$, h and j are as previously defined. The hydrosilation can be effected with various epoxy compounds such as allyl glycidyl ether, glycidyl acrylate, 4-vinylcyclohexene-1,2-oxide, etc., in the presence of a platinum catalyst by standard techniques.

As described in the literature, epoxy resins can also be modified in a number of standard ways such as reactions with amines, carboxylic acids, thiols, phenols, alcohols, etc., as shown in U.S. Pat. Nos. 2,935,488; 3,235,620; 3,369,055; 3,379,653; 3,398,211; 3,403,199; 3,563,850; 3,567,797; 3,677,995, etc. Further examples of epoxy resins which can be used as shown in the Encyclopedia of Polymer Science and Technology, Vol. 6, 1967, Interscience Publishers, New York, pp. 209–271.

I have found that improved compatibility between the above-described epoxy-siloxanes and diaryliodonium salts can be achieved, if diaryliodonium salts of the formula are used,

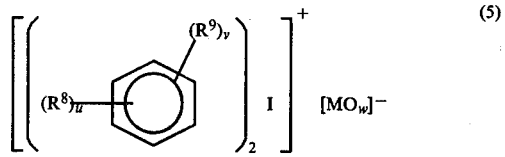 (5)

where M and Q are as previously defined, $R^8$ is a $C_{(4-20)}$ organo radical selected from alkyl, haloalkyl and branched alkyl, $R^9$ is selected from $C_{(1-3)}$ alkyl, $C_{(1-8)}$ alkoxy, nitro and halo, u is an integer having a value of from 1–4 inclusive, v is a whole number having a value of from 0–3 inclusive, w is an integer having a value of from 4–6 inclusive and the sum of u and v has a value of from 1–4 inclusive.

Radicals included by $R^8$ are, for example, butyl, pentyl, hexyl, octyl, dodecyl, tridecyl, hexadecyl, etc., halo derivatives of such radicals, for example, chlorobutyl, chlorodecyl, etc., branched alkyl such as ethylhexyl,

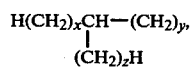

where x, y and z are integers having a value of 1 to 10 inclusive and their sum can be equal to 4 to 20 inclusive. Radicals included by $R^9$, are for example, methyl, ethyl, propyl, methoxy, ethoxy, chloro, bromo, fluoro, iodo, nitro, etc.

Included by the diaryliodonium salts of formula (5) are, for example,

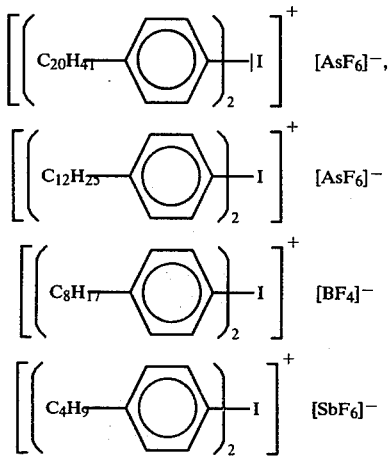

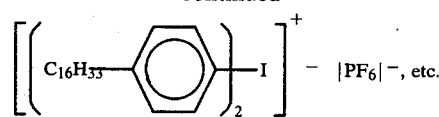

The curable compositions of the present invention can be made by blending the epoxy resin, which hereinafter will signify epoxy monomer, epoxy prepolymer, oxirane containing organic polymers or a mixture thereof, with an effective amount of the halonium salt. The resulting curable composition which can be in the form of a varnish having a viscosity of from 1 centipoise to 100,000 centipoises at 25° C. can be applied to a variety of substrates by conventional means and cured to the tack-free state within 1 second or less to 10 minutes or more. In other instances, where the epoxy resin is a solid, the curable composition can be a free flowing powder.

Depending upon the compatibility of the halonium salt with the epoxy resin, the halonium salt can be dissolved or dispersed therein along with an organic solvent such as nitromethane, acetonitrile, etc., prior to its incorporation. In instances where the epoxy resin is a solid, incorporation can be achieved by dry milling or by melt mixing. In situ preparation of the halonium salt by separate or simultaneous incorporation of halonium salt of the formula,

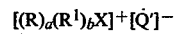

where R, $R^1$, X, a and b are as previously defined, and Q' is an anion such as $Cl^-$, $Br^-$, $F^-$, $I^-$, $HSO_4^-$, $CH_3SO_4^-$, $NO_3^-$, etc., with the salt of a Lewis Acid of the formula,

also has been found to be effective, where [MQ] is as defined above and M' is a metal cation such as $Na^+$, $K^+$, $Li^+$, $Ca^{++}$, $Mg^{++}$, $Fe^{++}$, $Ni^{++}$, $Co^{++}$, $Zn^{++}$. M' also can be an organic cation such as ammonium group, pyridinium group, etc. Examples of M'[MQ] are $NaBF_4$, $KAsF_6$, $NaSbF_6$, $KPF_6$, Experience has shown that the proportion of halonium salt of the epoxy resin can vary widely inasmuch as the salt is substantially inert, unless activated. Effective results can be achieved, for example, if a proportion of from 0.1% to 15% by weight of halonium salt is employed, based on the weight of curable composition. Higher or lower amounts can be used, however, depending upon factors such as the nature of epoxy resin, intensity of radiation, cure time desired, etc.

The curable compositions may contain inactive ingredients such as inorganic fillers, dyes, pigments, extenders, viscosity control agents, process aids, UV-screens, etc., in amounts of up to 100 parts filler per 100 of epoxy resin. The curable compositions can be applied to such substrates as metal, rubber, plastic, molded parts or films, paper, wood, glass cloth, concrete, ceramic, etc.

Some of the applications in which the curable compositions of the present invention can be used are, for example, protective, decorative and insulating coatings, potting compounds, printing inks, sealants, adhesives, photoresists, wire insulation, textile coatings, laminates, impregnated tapes, printing plates, etc.

Cure of the curable composition can be achieved by activating the halonium salt to provide the release of the Lewis Acid catalyst. Activation of the halonium salt can be achieved by heating the composition at a temperature in the range of from 150° C. to 250° C. Preferably cure can be achieved by exposing the curable composition to radiant energy such as electron beam or ultraviolet light. Electron beam cure can be effected at an accelerator voltage of from about 100 to 1000 KV. Cure of the compositions is preferably achieved by the use of UV irradiation having a wavelength of from 1849 Å to tp 4000 Å and an intensity of at least 5,000–80,000 microwatts per cm$^2$. The lamp systems used to generate such radiation can consist of ultraviolet lamps such as from 1 to 50 discharge lamps, for example, xenon, metallic halide, metallic arc, such as a low, medium or high pressure mercury vapor discharge lamp, etc., having an operating pressure of from a few millimeters to about 10 atmospheres, etc., can be employed. The lamps can include envelopes capable of transmitting light of a wave-length of from about 1849 Å to 4000 Å and preferably 2400 Å to 4000 Å. The lamp envelope can consist of quartz, such as Spectrocil, and also of Pyrex, etc. Typical lamps which can be employed for providing ultraviolet radiation are, for example, medium pressure mercury arcs, such as the GE H3T7 arc and the Hanovia 450 W arc lamp. The cures may be carried out with a combination of various lamps, some or all of which can operate in an inert atmosphere. When using UV lamps, the irradiation flux on the substrate can be at least 0.01 watts per square inch to effect cure of the epoxy resin within 1 to 20 seconds and permit the cure to be carried on continuously as, for example, in the curing of epoxy-coated steel strip to be taken up at a rate of from 100 to 600 feet per minute. The strip can be cut to a predetermined width for use as transformer laminates, etc. A combination of heat and light may be used to cure reactive compositions. Such as combination of heat and light may serve to reduce the overall cure time.

In order that those skilled in the art will be better able to practice the invention, the following examples are given by way of illustration and not by way of limitation. All parts are by weight.

EXAMPLE 1

There was added a cooled solution of about 100 ml of acetic anhydride and 70 ml of concentrated sulfuric acid to a suspension of 100 g of potassium iodate in 100 ml of acetic acid and 90 ml of benzene. During the addition, the mixture was stirred and maintained below 5° C. When the addition was complete, the reaction mixture was allowed to warm to room temperature and stirred for 48 hours. There was then added 400 ml of distilled water. The aqueous portion of the reaction mixture was extracted three times with diethylether and petroleum ether to remove unreacted organic materials. A pale yellow crystalline product formed upon addition of ammonium chloride to the aqueous reaction mixture. There was obtained 48% yield of diphenyliodonium chloride having a m.p. of 180°–185° C. The cure salt had a m.p. of 228°–229° C.

A mixture of 20 g of moist, freshly prepared Ag$_2$O, 10 ml of water and 31.6 g of diphenyliodonium chloride was ground together in a slurry. The wet mixture was filtered and washed with water to produce 360 ml of filtrate. The filtrate was cooled until a substantial amount of the solution had frozen. There was slowly added 25 ml 45–50% HBF$_4$ cooled to −15° C. The cold solution was stirred and allowed to warm to room temperature. A white crystalline solid separated and was collected by filtration. There was obtained a 60% yield of diphenyliodonium fluoroborate, m.p. 136° C. when the solid was dried overnight in vacuo at 60° C.

A curable composition was prepared by dissolving 0.05 part of diphenyliodonium tetrafluoroborate in a small amount of acetonitrile and mixing the resulting solution in 5 parts of 4-vinylcyclohexene dioxide.

The viscosity of the resulting curable composition was found to be initially about 6 centipoises at 25° C. It did not change substantially after several months exposure under normal room lighting.

A portion of the curable composition was applied as a 0.1 mil film onto a steel strip. The treated steel surface was exposed 15 seconds to the ultraviolet radiation of an H3T7 lamp at a distance of 2 inches. A clear tack-free film was formed which showed no signs of bubbles or other imperfections.

The above treated strip was then immersed in 10 C hydrocarbon oil for 48 hours at 120° C. to determine its hydrolytic stability in accordance with IFT test ASTM D971-50 Interfacial Tension of Oil Against Water, shown on page 322 of the 1970 Annual Book of ASTM Standards, part 17 (November). The initial reading of the oil was about 39.0 dynes/cm. After the test the oil showed an interfacial tension reading of 38. In order to pass a reading of at least 30 is required.

EXAMPLE 2

The procedure of Example 1 was repeated for preparing an aromatic halonium salt using diphenyliodonium chloride. In this preparation, fluoroboric acid was replaced by 25 ml (60%) hexafluorophosphoric acid. There was obtained a 74% yield of diphenyliodonium hexafluorophosphate having a m.p. of 139°–141° C.

A curable composition was prepared following the same procedure as Example 1. Comparable results were achieved with respect to its ability to resist change in viscosity over an extended period of time under normal atmospheric conditions. In addition, satisfactory IFT values were also obtained.

EXAMPLE 3

A curable composition was prepared using a 40:60 solution of 4-vinylcyclohexene dioxide and a novolak-epoxy resin and adding 2% by weight of diphenyliodonium tetrafluoroborate in a small amount of nitromethane.

The curable composition was spread on a glass plate. A mask was then used to cover the treated glass. After irradiation under an H3T7 lamp for 1.5 minutes, the glass was washed with isopropanol. The unexposed portions were washed completely away leaving a negative image of the mask. When the same procedure is repeated using a steel plate as the substrate, the product is useful for the fabrication of printing plates.

EXAMPLE 4

Several curable compositions were prepared in accordance with the procedure shown in Example 1 using 4-vinylcyclohexene dioxide and about 3% by weight of the halonium salt. Various cure times were experienced when the compositions were applied onto a glass substrate and cured at a distance of four inches from a Ge H3T7 lamp. The following shows the halonium salt used, its m.p. and the cure times:

| Halonium Salt | | | | Cure Time* (min.) |
|---|---|---|---|---|
| | Cation | Anion | Mp.(°C.) | |
| I | C₆H₅–I⁺–C₆H₅ | BF₄⁻ | 136 | 0.5 |
| II | C₆H₅–I⁺–C₆H₅ | PF₆⁻ | 138–141 | 0.5 |
| III | C₆H₅–I⁺–C₆H₅ | SbF₆⁻ | 57–58 imp. | 0.5 |
| IV | C₆H₅–I⁺–C₆H₄–OCH₃ | BF₄⁻ | 96–100 | 1 |
| V | CH₃–C₆H₄–I⁺–C₆H₄–CH₃ | BF₄⁻ | 95–100 | 0.5 |
| VI | C₆H₅–I⁺–C₆H₄(NO₂) | BF₄⁻ | 133–135 | 1 |

*Time required to cure a 2 mil film containing 3% of the salt at a distance of 4 inches from a G.E. H3T7 lamp.

EXAMPLE 5

To 10 g limonene dioxide were added 0.32 g diphenyliodonium chloride and 0.21 g sodium hexafluoroarsenate. This mixture was heated for 20 minutes at 50° C. to achieve metathesis. The salts were allowed to settle and the clear supernatent liquid was drawn off. The sensitized epoxy compound was applied to a steel strip to a thickness of 2 mil and exposed to UV light as described above. Cure took place in 30 seconds. A tough film having good adhesion to the steel plate was obtained.

EXAMPLE 6

Three parts of diphenyliodonium fluoroborate were ground to a fine powder and tumbled for 30 minutes with 97 parts of Reichhold Epotuf® 37-834 powder coating resin. The powder blend was then electrostatically sprayed onto 3 in×6 in steel samples to form a 2 mil coating using a GEMA model 171 spray gun. Subsequently, the samples were heated briefly to 150° C. to fuse the powder and then exposed while hot to a G.E. H3T6 medium pressure mercury arc lamp at a distance of 3 inches. Cured samples were obtained after 30 seconds exposure.

EXAMPLE 7

Three parts by weight of di-p-tolyl iodonium fluoroborate were added to 97 parts of (3,4-epoxycyclohexyl)-methyl-3,4-epoxycyclohexanecarboxylate. The epoxy resin was then used to impregnate a 1 inch woven glass tape. After winding two turns of the tape onto a 4 in diameter drum, the tape was cured to a rigid glass band by rotating the dum under a GE H3T7 lamp at a distance of 4 inches for 2 minutes. The banding tapes thus prepared can be used as restraining bands in motors and generators.

The above resin was used to impregnate woven glass cloth. Two 6 in×6 in squares of the glass cloth were stacked on top of one another and cured for 1 minute on each side. A rigid composite was obtained which is useful for circuit board applications.

A portion of the above mixture was used to impregnate glass roving. The treated glass was then wound onto a 3 in dia. drum to a thickness of about 5 mils. The drum was then rotated beneath a GE H3T7 lamp at a distance of 3 inches for 5 minutes. A measurement of the intensity of the lamp showed that it was approximately 200 watts/sq. inch. When the cured winding was removed from the drum, it was rigid and fully cured. A typical use for such a cured winding is as a spool for electrically conducting wire.

EXAMPLE 8

A mixture was prepared consisting of 14.5 g (0.25 mole) allyl glycidyl ether, 10 mg. t-butyl-catechol, and 3 drops chloroplatinic acid in octyl alcohol. The reaction mixture was heated to 50° C. in a water bath and then 13.0 g of a polydimethyl siloxane resin containing 0.89% by weight Si-H groups was added dropwise by means of a dropping funnel. Immediate exothermic reaction took place with the temperature rising to 65° C. Reaction proceeded smoothly at this temperature giving a clear resin.

Three parts by weight of 4-methoxydiphenyliodonium fluoroborate dissolved in a small amount of methylene chloride was added to 97 parts of the above silicone epoxy resin. A 2 mil film of the sensitized resin was drawn on a steel plate and then exposed to UV light from a GE H3T7 lamp at a distance fo six inches. The film was tack-free within 10–15 seconds. A small amount of silica was added to the sensitized resin to produce a thixotropic mixture and the resin cured as described previously. A tough, rubbery coating resulted.

EXAMPLE 9

A solution of 3 parts of 4-methoxydiphenyliodonium fluoroborate dissolved in 20 parts of 4-vinyl-cyclohexene dioxide was added to 80 parts of a glycidyl methacrylate-methyl methacrylate copolymer having a molecular weight of 8,500 and a glycidyl acrylate content of 5% by weight. This mixture was mixed by rolling it in a glass bottle on a ball mill overnight. The viscous solution was knife coated onto a glass plate to give a 2 mil film which then irradiated at a distance of six inches from a GE H3T7 lamp, gave a clear hard coating in 10 seconds. The film was highly crosslinked and insoluble in all common solvents.

EXAMPLE 10

Three parts of diphenyliodonium hexafluoroarsenate were dissolved in 6.7 parts of methylene chloride and the solution added to 97 parts glycidyl acrylate. A 3 part aliquot of this highly fluid mixture was placed in an aluminum cup and then exposed to the ultraviolet irradiation of a H3T7 lamp using a water filter. The cure time was 15 seconds. Subsequent analysis showed that the conversion to polymer was greater than 95%. A hard glossy resin was obtained.

EXAMPLE 11

A blend was prepared using equal parts of 4-vinylcyclohexene dioxide and 3,4-epoxycyclohexyl methyl-3,4-epoxycyclohexanecarboxylate. To this blend were added four parts of diphenyliodonium fluoroborate. An aliquot of the above sensitized resin was spread onto a sheet of Lexan® polycarbonate using a draw-down blade to give a 0.5 mil film. The film was cured as described in Example 3 for 20 seconds giving a clear hard coating which provides mar and solvent resistance for the substrate polymer.

EXAMPLE 12

A mixture of 50 parts bisphenol-A-diglycidyl ether and 50 parts 3,4-epoxy-cyclohexyl methyl-3,4-epoxycyclohexanecarboxylate was stirred until homogeneous and then 3 parts by weight diphenyliodonium hexafluoroantimonate in a small amount of methylene chloride was added and the solution thoroughly mixed. A portion of the above sensitized solution was coated onto a steel plate using a 0.2 mil drawbar. The plate was then irradiated for 10 seconds using a Ge H3T7 mercury arc lamp at a distance of six inches. The completely cured, hard, glossy film had excellent adhesion to the steel and could not be removed by rubbing it with acetone.

EXAMPLE 13

A blend of epoxy resins consisting of 50 parts 4-vinylcyclohexane dioxide, 40 parts of a novolak-epoxy resin having an epoxy equivalent weight of 172–178 and 10 parts n-decylglycidyl ether were thoroughly mixed together. A 100 part aliquot was taken and 1 part diphenyliodonium hexafluorophosphate was added and the resulting mixture stirred until the catalyst had dissolved. When the above mixture was coated onto a 3 in×6 in panel and then exposed to a 450 watt medium pressure mercury arc lamp at a distance of 3 inches, a glossy, dry coating was obtained in 3 seconds. The coating withstood attack by hot boiling water for four hours and could not be removed by rubbing with acetone.

EXAMPLE 14

There was added 1 g of di-p-tolyliodonium fluoroborate to a mixture of 40 g limonene dioxide and 10 g of a solid multifunctional aromatic glycidyl ether having an epoxy equivalent weight of 210–240. The mixture was stirred at 50° C. for 1 hour to produce a homogeneous solution of the components. When the mixture was coated onto a glass plate using a 0.5 mil drawbar, a hard, adherent, cured film was produced by irradiating the sample for 5 seconds at a distance of 3 inches from a GE H3T7 lamp which has an intensity of 200 watts/sq. inch.

EXAMPLE 15

There was added 0.2 part p-methoxydiphenyliodonium fluoroborate in 2 parts 4-vinylcyclohexene dioxide to 10 parts of an epoxidized butadiene resin. After mixing, a 1 mil coating of the resulting mixture was applied onto a 1/16 inch thick glass plate. Another plate of glass was placed on top of the first and this assembly exposed to a Ge H3T7 medium pressure mercury arc lamp having an intensity of 200 watts/sq. inc. at a distance of 3 inches. The total time of exposure was 1 minute. The glass plates were permanently bonded together and the glass laminate could be used as a shatterproof windshield for automobiles.

EXAMPLE 16

A mixture was prepared consisting of by weight 67% of a novolak-epoxy resin having an epoxy equivalent weight of 172–178, 33% 4-vinylcyclohexene dioxide, 0.5% of a surface active agent, and 1% diphenyliodonium hexafluoroarsenate. The mixture was applied as a 0.1 mil film to 3 in×6 in steel plates. The treated plates were exposed for 20 seconds at a distance of 4 inches from a GE H3T7 medium pressure mercury arc lamp. Panels were subsequently immersed for 5 hours at room temperature in methylene chloride; others were immersed for 4 hours in acetone. In all cases, no visible signs of attack on the coating by these agents were observed. The panels were baked for 1 hour at 160° C., then tests were run separately in boiling 5% KOH solution for 30 minutes and in boiling distilled water for 4 hours. At the end of these tests, the coatings were intact and showed no signs of degradation.

EXAMPLE 17

There was added 0.2 part of 4-vinylcyclohexene-1,2-oxide to 34 parts of a hydrogen terminated polydiphenylsoloxane having a viscosity of about 16,550 centipoises while the resulting mixture was stirred. There was then added 0.001 parts of platinum in the form of the reaction product of chloroplatinic acid and chloroplatinic acid hexahydrate and octyl alcohol as shown by U.S. Pat. No. 3,220,972, Lamoreaux, assigned to the same assignee as the present invention. The reaction mixture was then heated to 60° C. and maintained at this temperature for three hours. The mixture was then stripped under reduced pressure of unreacted epoxy functional organic material. Based on method of preparation, there was obtained an epoxy functional silicone resin consisting essentially of chemically combined dimethylsiloxy units and terminated with dimethylethylcyclohexene-1,2-oxide siloxy units.

UV curable mixtures were then prepared from aliquots of epoxy silicone fluid with various diarylhalonium salt photoinitiators which were utilized at 2% by weight respectively. The respective mixtures were applied as 2 mil films on glass plates and then cured using a GE H3T7 medium pressure mercury arc lamp at a distance of 7 inches from the sample.

| Halonium Salt | Cure Time (min) |
| --- | --- |
| $(\text{C}_6\text{H}_5)_2\text{I}^+ \text{AsF}_6^-$ | >3 min |
| $(\text{CH}_3\text{-C}_6\text{H}_4)_2\text{I}^+ \text{AsF}_6^-$ | >3 min |
| $(\text{Cl-C}_6\text{H}_4)_2\text{I}^+ \text{PF}_6^-$ | >3 min |
| $(\text{C}_4\text{H}_9\text{-C}_6\text{H}_4)_2\text{I}^+ \text{AsF}_6^-$ | 3 sec |
| $(\text{C}_7\text{H}_{15}\text{-C}_6\text{H}_4)_2\text{I}^+ \text{AsF}_6^-$ | 3 sec |

The above results show that as the length of the alkyl group increased on the phenyl radical of the diaryliodonium salt improvement in cure time was effected. The above cure time was determined when the applied curable mixture was converted to a tack-free film.

EXAMPLE 18

There was added about 183 parts of concentrated sulfuric acid to a mixture with stirring consisting of 16.1 parts of iodosobenzene diacetate, 17.6 parts of n-heptyl benzene and 52 parts of acetic anhydride at a temperature of −20° C. The sulfuric acid was added dropwise while the mixture was vigorously stirred. After the sulfuric acid addition, the mixture was stirred for an additional hour. The mixture was then poured into 500 parts of ice to produce a two phase mixture. There was added 11.4 parts of potassium hexafluoro arsenate to the mixture and it was stirred for 30 minutes. The upper aqueous layer was then removed by decantation. The remaining oil was washed twice with about 50 part portions of water. The product was then washed thoroughly with petroleum ether. There was obtained 25 parts of bis(4-n-heptylphenyl) iodonium hexafluoroarsenate, based on method of preparation.

A photocurable mixture consisting of the epoxy functional silicone fluid of Example 17 having 3% by weight of the above bis(heptylphenyl) substituted iodonium salt was found to cure in 5 seconds in accordance with the procedure of Example 17.

EXAMPLE 19

There was slowly added with stirring, 36 parts of concentrated sulfuric acid to a mixture cooled to $-10°$ C. consisting of 25 parts of potassium iodate, 100 parts of phenyl nonadecane, 55 parts of acetic anhydride, and 80 parts of methylene chloride. The reaction temperature was maintained at 12°–13° C. during the addition. After the addition was completed, the reaction mixture was allowed to stir at 12°–13° C. for four hours and slowly warmed up to room temperature and then allowed to stand for an additional 8 hours. There was then added 100 parts of water to the mixture and it became a light orange solution. There was then added 30 parts of sodium hexafluoroantimonate to the solution as an aqueous mixture. A precipitate was formed which was collected by filtration. The product was then purified by reprecipitation from isopropanol. Based on method of preparation, there was obtained bis(-nonadecylphenyl)iodonium hexafluoroantimonate at a yield of about 50% by weight.

The above diaryliodonium salt was then utilized in accordance with the procedure shown for Example 17. Substantially similar cure results were obtained of the epoxy resin showing that improved compatibility was achieved by use of the higher alkyl substituted benzene.

Although the above examples are directed to only a few of the very many variables of the present invention, it should be understood that the present invention is directed to a much broader class of UV-curable compositions comprising epoxy siloxanes comprising organo siloxane units of formula (2) chemically combined with epoxy siloxane units of formula (3) and in further combination with alkyl substituted diaryliodonium salts of formula (4). The preferred diaryliodonium salts of formula (4) are hexafluoro metal or metalloid diaryliodonium salts of the formula,

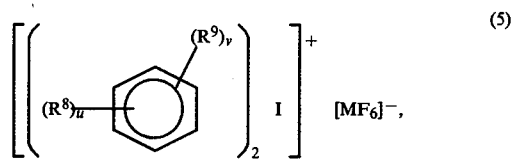

where $R^8$, $R^9$, u and v are as previously defined.

What I claim as new and desire to secure by Letters Patent of the United States is:

1. A diaryliodonium salt having the formula,

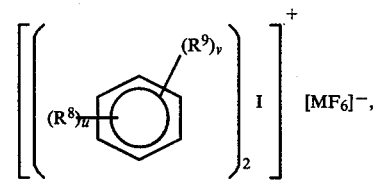

where $R^8$ is a $C_{19}$ organo radical selected from alkyl, haloalkyl and branched alkyl, $R^9$ is selected from $C_{(1-3)}$ alkyl, $C_{(1-8)}$ alkoxy, nitro and halo, M is a metal or metalloid selected from phosphorus, antimony and arsenic, u is an integer having a value of 1 to 4 inclusive, v is a whole number having a value of 0 to 3 inclusive and the sum of u and v has a value of from 1 to 4 inclusive.

2. A diaryliodonium salt of the formula,

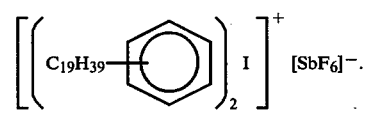

* * * * *